US00PP35038P2

(12) United States Plant Patent
van Rijn

(10) Patent No.: US PP35,038 P2
(45) Date of Patent: Mar. 14, 2023

(54) ***CELOSIA* PLANT NAMED 'ZANCESHA'**

(50) Latin Name: *Celosia argentea*
Varietal Denomination: 'Zancesha'

(71) Applicant: Bernadette Geertruida Maria van Rijn, Aalsmeer (NL)

(72) Inventor: Bernadette Geertruida Maria van Rijn, Aalsmeer (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 17/952,889

(22) Filed: Sep. 26, 2022

(51) Int. Cl.
*A01H 6/02* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — C. Anne Whealy

(57) ABSTRACT

A new and distinct cultivar of *Celosia* plant named 'Zancesha', characterized by its upright plant habit; vigorous growth habit and rapid growth rate; freely branching habit; dark purplish red-colored leaves; freely flowering habit; purplish red-colored flowers arranged on spicate-type inflorescences; and good container performance.

3 Drawing Sheets

Figure 1:
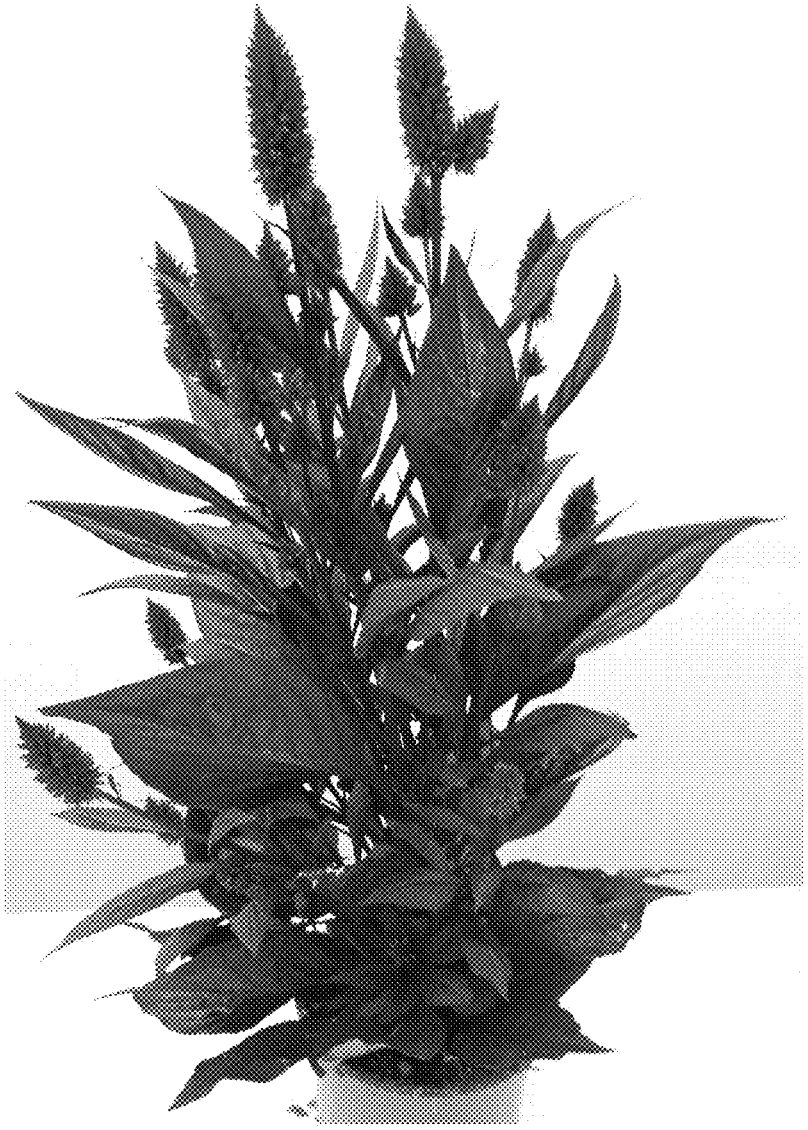

Botanical designation: *Celosia argentea.*
Cultivar denomination: 'ZANCESHA'.

CROSS-REFERENCED TO CLOSELY-RELATED APPLICATIONS & CLAIM TO FOREIGN PRIORITY

An European Plant Breeder's Rights application was filed for the *Celosia* 'Zancesha' on Nov. 4, 2021, application number 2021/2773. Foreign priority is claimed to this previously filed application.

BACKGROUND OF THE INVENTION

The present invention relates to a new and distinct cultivar of *Celosia* plant, botanically known as *Celosia argentea* and hereinafter referred to by the name 'Zancesha'.

The new *Celosia* plant is a product of a planned breeding program conducted by the Inventor in Rijsenhout, The Netherlands. The objective of the breeding program is to create new compact and uniform *Celosia* plants with attractive and unique leaf and flower coloration.

The new *Celosia* plant originated from a cross-pollination made by the Inventor in Rijsenhout, The Netherlands in October, 2017 of a proprietary *Celosia argentea* selection identified as code number 15-0131, not patented, as the female, or seed, parent with a mixture of pollen from a number of proprietary *Celosia argentea* selections, as the male, or pollen, parent. The new *Celosia* plant was discovered and selected by the Inventor as a single flowering plant from within the progeny of the stated cross-pollination in a controlled greenhouse environment in Rijsenhout, The Netherlands in June, 2018.

Asexual reproduction of the new *Celosia* plant by cuttings in a controlled greenhouse environment in Rijsenhout, The Netherlands since August, 2018 has shown that the unique features of this new *Celosia* plant are stable and reproduced true to type in successive generations.

SUMMARY OF THE INVENTION

Plants of the new *Celosia* have not been observed under all possible environmental conditions and cultural practices.

The phenotype may vary somewhat with variations in environmental such as temperature and light intensity without, however, any variance in genotype.

The following traits have been repeatedly observed and are determined to be the unique characteristics of 'Zancesha'. These characteristics in combination distinguish 'Zancesha' as a new and *Celosia* plant:

1. Upright plant habit.
2. Vigorous growth habit and rapid growth rate.
3. Freely branching habit.
4. Dark purplish red-colored leaves.
5. Freely flowering habit.
6. Purplish red-colored flowers arranged on spicate-type inflorescences.
7. Good container performance.

Plants of the new *Celosia* differ primarily from plants of the female parent selection in leaf color as plants of the new *Celosia* have dark purplish red-colored leaves whereas plants of the female parent selection have green-colored leaves with random purple-colored spots.

Plants of the new *Celosia* can be compared to plants of *Celosia hybrida* 'Zancemepur', disclosed in U.S. Plant Pat. No. 31,267. In side-by-side comparisons, plants of the new *Celosia* and 'Zancemepur' differ primarily in the following characteristics:

1. Plants of the new *Celosia* have dark purplish red-colored leaves whereas plants of 'Zancemepur' have medium green-colored leaves with random dark purplish red-colored spots.
2. Flowers of plants of the new *Celosia* are slightly darker purplish red than flowers of plants of 'Zancemepur'.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet (FIG. 1) comprises a side perspective view of a typical flowering plant of 'Zancesha' grown in a container.

Figure 2:
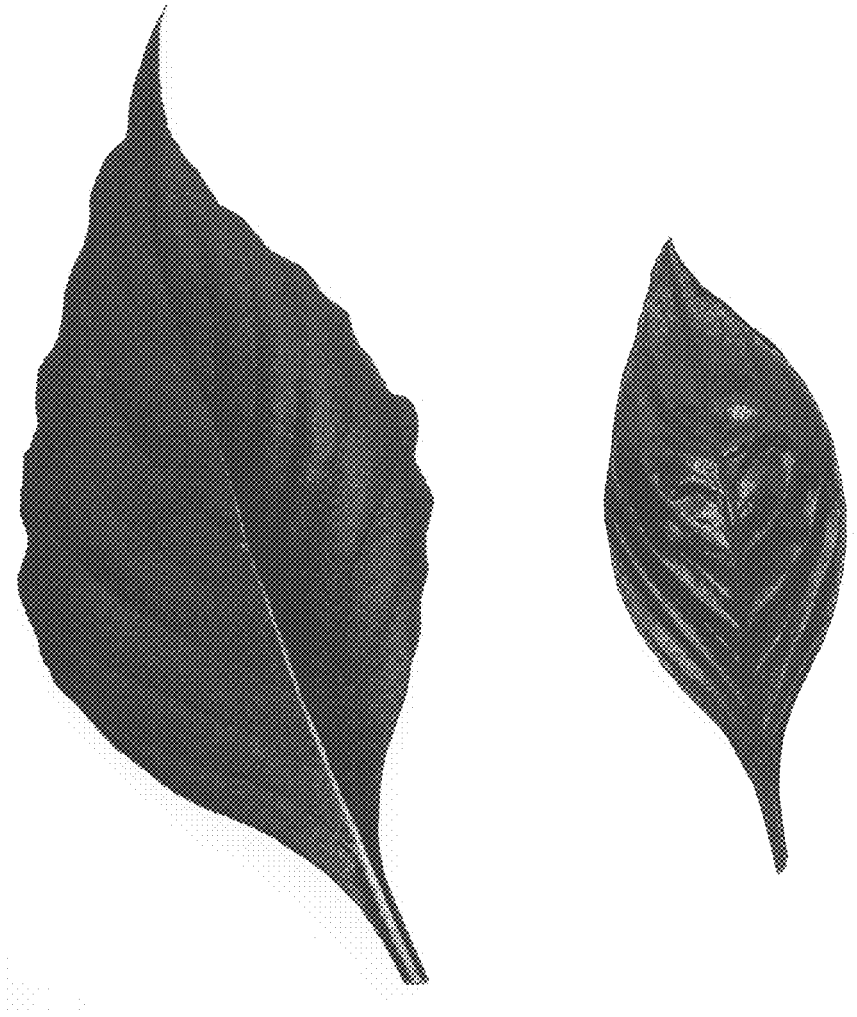

The photograph on the second sheet (FIG. 2) is a close-up view of typical fully expanded (left) and developing (right) leaves of 'Zancesha'.

Figure 3:
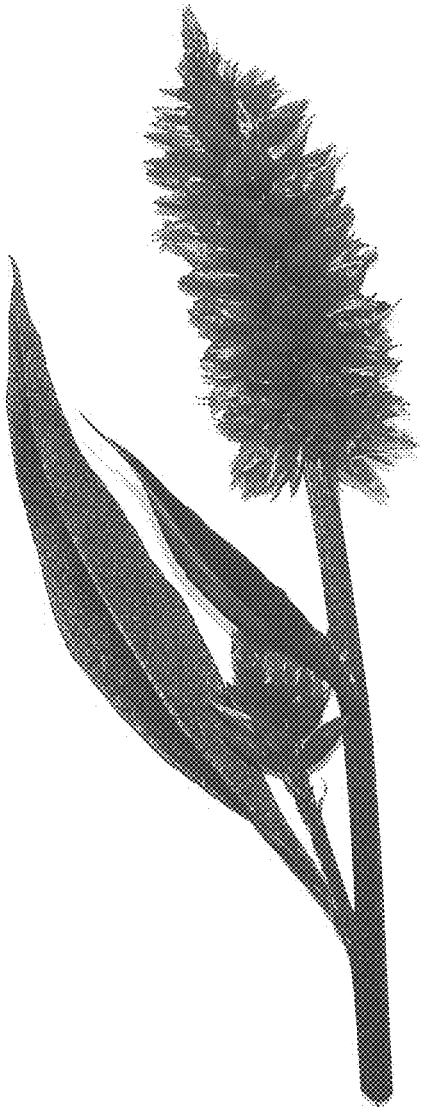

The photograph on the third sheet (FIG. 3) is a close up view of a typical flowering stem of 'Zancesha'.

DETAILED BOTANICAL DESCRIPTION

The aforementioned photographs and following observations, measurements and values describe plants grown during the early spring in 9-cm containers in a glass-covered greenhouse in Rijsenhout, The Netherlands and under cultural practices typical of commercial *Celosia* production. During the production of the plants, day and night temperatures ranged from 20° C. to 22° C. Plants were grown under photoinductive long nyctoperiods, pinched one time about 2.5 weeks after planting and were ten weeks old when the photographs and description were taken. In the following description, color references are made to The Royal Horticultural Society Colour Chart, 2015 Edition, except where general terms of ordinary dictionary significance are used.

Botanical classification: *Celosia argentea* 'Zancesha'.

Parentage:

*Female, or seed, parent*.—Proprietary *Celosia argentea* selection identified as code number 15-0131, not patented.

*Male, or pollen, parent*.—A mixture of pollen from a number of proprietary *Celosia argentea* selections, not patented.

Propagation:

*Type*.—By terminal cuttings.

*Time to initiate roots, summer*.—About 12 days at temperatures about 21° C.

*Time to produce a rooted young plant, summer*.—About 19 days at temperatures about 21° C.

*Root description*.—Fine, fibrous and fleshy; close to 199D in color.

*Rooting habit*.—Freely branching; dense.

Plant description:

*Plant form and growth habit*.—Herbaceous annual typically grown as a potted plant; upright plant habit; freely branching habit with about five to six lateral branches developing per plant; vigorous growth habit and rapid growth rate.

*Plant height*.—About 35 cm to 40 cm.

*Plant width (spread)*.—About 20 cm to 25 cm.

*Lateral branches*.—Length: About 23 cm to 33 cm. Diameter: About 2.5 mm to 4 mm. Internode length: About 1.5 cm to 2.5 cm. Texture and luster: Ribbed, glabrous; matte. Color: Close to 187A.

Leaf description:

*Arrangement*.—Alternate; simple.

*Length*.—About 7 cm to 14 cm.

*Width*.—About 2 cm to 5 cm.

*Shape*.—Elliptic to broadly elliptic.

*Apex*.—Acuminate.

*Base*.—Attenuate to truncate.

*Margin*.—Entire.

*Texture, upper and lower surfaces*.—Smooth, glabrous.

*Venation pattern*.—Pinnate.

*Color*.—Developing leaves, upper surface: Close to N79A. Developing leaves, lower surface: Close to N79B. Fully expanded leaves, upper surface: Close to N79A; venation, close to 73D. Fully expanded leaves, lower surface: Close to 187C; venation, close to N79C.

*Petioles*.—Length: About 1 cm to 2 cm. Diameter: About 2 mm to 3 mm. Texture, upper and lower surfaces: Smooth, glabrous. Color, upper surface: Close to 73D. Color, lower surface: Close to N79C.

Flower description:

*Flower type and flowering habit*.—Single elliptical flowers arranged in terminal and axillary spikes; spicate-type inflorescences; flowers face mostly upright; freely flowering habit, about 80 to 150 flowers per inflorescence and about 4,000 flowers developing per plant during the flowering season.

*Fragrance*.—None detected.

*Natural flowering season*.—Plants begin flowering about 5.5 weeks after planting; in the garden, plants flower continuously during the summer in The Netherlands.

*Postproduction longevity*.—Inflorescences last about two months on the plant; flowers persistent.

*Inflorescence height*.—About 3.5 cm to 5 cm.

*Inflorescence diameter*.—About 1.5 cm to 2 cm.

*Flower diameter*.—About 2 mm.

*Flower depth*.—About 6 mm.

*Flower buds*.—Length: About 3 mm. Diameter: About 1 mm. Shape: Elliptic. Color: Close to 72A.

*Petals*.—None observed.

*Sepals*.—Quantity per flower: Typically five. Length: About 5 mm. Width: About 1 mm. Shape: Lanceolate. Apex: Acute. Base: Attenuate. Margin: Entire. Texture, upper and lower surfaces: Smooth, glabrous. Color: When opening and fully opened, upper surface: Close to 72A; color becoming closer to 186A with subsequent development. When opening and fully opened, lower surface: Close to 72A; color becoming closer to 186A with subsequent development.

*Pedicels*.—Length: About 1 mm. Diameter: About 2 mm. Angle: About 45° from vertical. Strength: Weak; flexible. Texture: Smooth, glabrous. Color: Close to 187A.

*Reproductive organs*.—Stamens: Quantity per flower: Typically five. Filament length: About 2 mm. Filament color: Close to N79C. Anther length: About 2 mm. Anther color: Close to 76C. Pollen amount: Moderate. Pollen color: Close to 161D. Pistils: Quantity per flower: One. Pistil length: About 4 mm. Style length: About 3 mm. Style color: Close to N79C. Stigma color: Close to N79C. Ovary color: Close to N79A.

*Seeds*.—Length: About 1.5 mm. Diameter: About 1.5 mm. Color: Close to 202A.

Pathogen & pest resistance: To date, plants of the new *Celosia* have not been noted to be resistant to pathogens and pests common to *Celosia* plants.

Garden performance: Plants of the new *Celosia* have been observed to have good garden performance and tolerate rain and temperatures ranging from about 10° C. to 30° C.

It is claimed:

1. A new and distinct *Celosia* plant named 'Zancesha' as illustrated and described.

* * * * *